United States Patent

Bierdel-Willkommen et al.

[11] Patent Number: 5,916,591
[45] Date of Patent: *Jun. 29, 1999

[54] SOFT GELATIN CAPSULES

[75] Inventors: Elvira Bierdel-Willkommen, Sindelfingen; Clemens Sambale, Böhl-Iggelheim; Wolfgang Hähnlein, Freinsheim, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/602,029

[22] Filed: Feb. 15, 1996

[30] Foreign Application Priority Data

Feb. 24, 1995 [DE] Germany .................. 195 06 569

[51] Int. Cl.⁶ ...................................... A61K 9/48
[52] U.S. Cl. .................. 424/456; 424/451; 424/455; 514/951; 514/962
[58] Field of Search .................. 424/456, 451, 424/455; 514/951, 962

[56] References Cited

U.S. PATENT DOCUMENTS

| | | | |
|---|---|---|---|
| 3,427,378 | 2/1969 | Henderson | 424/14 |
| 5,595,758 | 1/1997 | Adusumilli et al. | 424/456 |

FOREIGN PATENT DOCUMENTS

| | | |
|---|---|---|
| 1 267 841 | 4/1990 | Canada . |
| 65 193 | 11/1982 | European Pat. Off. . |
| 184 942 | 6/1986 | European Pat. Off. . |
| 337 509 | 10/1989 | European Pat. Off. . |
| 374 359 | 6/1990 | European Pat. Off. . |

OTHER PUBLICATIONS

Lehrbuch der Pharmazeutischen Technologie, Voight, 1987, pp. 230–233 (No Translation).

*Primary Examiner*—Fred Zitomer
*Attorney, Agent, or Firm*—Keil & Weinkauf

[57] ABSTRACT

Soft gelatin capsules consisting of capsule shell and capsule filling, where the capsule filling comprises one or more water-insoluble active ingredients) in the form of a powdered product.

8 Claims, No Drawings

SOFT GELATIN CAPSULES

The present invention relates to soft gelatin capsules consisting of capsule shell and capsule filling.

It is generally known that active ingredients can be administered in soft gelatin capsules, see, for example, R. Voigt, Lehrbuch der pharmazeutischen Technologie, VCH, Weinheim 1987, pages 230 et seq., or EP-A-337 509. In such cases the form of the filling materials is important both for the production and for the stability and efficacy of the soft gelatin capsules.

In general, liquid or semisolid filling materials are encapsulated in the production of soft gelatin capsules. If the active ingredients are in solid form, they must be dissolved or suspended in a suitable liquid vehicle or be converted into a paste using thickeners. In many cases, the active ingredients, such as solid, water-insoluble active ingredients, especially retinoids, carotenoids or vitamins, have insufficient solubility in the liquid vehicles which can be used for these purposes. Dispersions therefore result, and the active ingredients readily sediment in these so that the dispersions can no longer be pumped. Moreover the pastes produced with thickeners have the disadvantage of lack of pumpability.

Another criterion for the use of soft gelatin capsules is the efficacy of the encapsulated filling material. The bioavailability of the active ingredients is important for the efficacy, the aim being to achieve maximum bioavailability.

It is an object of the present invention to provide soft gelatin capsules with which solid, water-insoluble, maximally bioavailable active ingredients can be formulated in the capsule filling so that no sedimentation problems occur during production, and the capsule filling remains pumpable.

We have found that this object is achieved with soft gelatin capsules consisting of capsule shell and capsule filling whose capsule filling comprises one or more active ingredient(s) which is (are) insoluble in water at 20° C., in the form of a powdered product with the following particle size distribution: <10% <5 $\mu$m and <1% >400 $\mu$m. This means that less than 10% of the particles in the powdered product have a particle size below 5 $\mu$m and less than 1% of the particles have a particle size above 400 $\mu$m.

It has emerged, surprisingly, that the soft gelatin capsules according to the invention can be produced without sedimentation of the active ingredient dispersion when the active ingredient is in the form of a dispersion of a powdered product with the stated particle size distribution, it being possible to use active ingredients with high bioavailability, and the bioavailability being retained.

The particle size distribution of the powdered product preferably has the following values: <10% <10 $\mu$m and <1% >350 $\mu$m, in particular <5% <5 $\mu$m and <1% >320 $\mu$m.

The maximum of the particle size distribution can be at from 40 to 100 $\mu$m.

The powdered product preferably comprises a colloid beside the solid, water-insoluble active ingredient with the stated particle size distribution. The production of such powdered products is known per se and is described, for example, in EP-B 065 193, to which express reference is made. Colloids which can be present are swellable colloids such as gelatin, starch, dextrin, pectin, gum arabic, casein, caseinate, soybean protein or mixtures thereof. However, it is also possible to use polyvinyl alcohol, polyvinylpyrrolidone, methylcellulose, carboxymethylcellulose, hydroxypropylcellulose and alginates. For further details, reference is made to R. A. Morton, Fat Soluble Vitamins, intern. Encyclopedia of Food and Nutrition, Volume 9, Pergamon Press 1970, pages 128 to 131. To increase the mechanical stability of the powdered product, it is expedient to add to the colloid a plasticizer such as sugar or sugar alcohols, eg. sucrose, glucose, lactose, invert sugar, sorbitol, mannitol or glycerol. The ratio of colloid to active ingredient and plasticizer is generally chosen so that the resulting powdered product contains 0.5–25% by weight, preferably 1–20% by weight, of the active ingredient, 10–50% by weight of the colloid and 20–70% by weight of the plasticizer, based on the dry weight of the powder.

To increase the stability of the active ingredient to oxidative breakdown, it is advantageous to add to the powdered product stabilizers such as $\alpha$-tocopherol, butylated hydroxytoluene, butylated hydroxyanisole or ethoxyquluin.

A particularly suitable colloid has proven to be a soybean protein/carbohydrate or a gelatin/carbohydrate matrix in which the solid active ingredient is embedded. If the solid active ingredient is a retinoid, carotenoid or vitamin, the powdered product forms a fine-particle dispersion, for example in cold water.

The carotenoids which can be present in the soft gelatin capsules are the known, available, natural or synthetic representatives of this class of compounds, which can also be used as coloring agents, eg. carotene, lycopene, bixin, zeaxanthin, cryptoxanthin, citranaxanthin, lutein, canthaxanthin, astaxanthin, $\beta$-apo-4'-carotenal, $\beta$-apo-8'-carotenal, $\beta$-apo-12'-carotenal, $\beta$-apo-8'-carotenoic acid and esters of hydroxyl- and carboxyl-containing representatives of this group, eg. the lower alkyl esters and, preferably, the methyl and ethyl esters. The representatives which are readily obtainable industrially are particularly preferred, such as $\beta$-carotene, canthaxanthin, $\beta$-apo-8'-carotenal and $\beta$-apo-8'-carotenoic esters. Soft gelatin capsules which contain $\beta$-carotene as active ingredient in the powdered product are very particularly preferred.

Retinoids mean, in particular, all-trans-retinoic acid, 13-cis-retinoic acid and the esters and amides of these acids. The specific formulae of these retinoids are described by D. L. Newton, W. R. Henderson and M. B. Sporn in Cancer Research 40, (1980) 3413–3425, so that reference is made thereto.

Vitamins present in the powdered products of the soft gelatin capsules according to the invention are, in particular, vitamin A, vitamin E (eg. as acetate), vitamin $B_1$, vitamin $B_2$, vitamin $B_6$ and/or $B_{12}$.

The powdered products are also referred to as dry powders.

Besides the powdered products, the soft gelatin capsules can also contain other active ingredients, eg. from said groups of carotenoids, retinoids and/or vitamins, the substances detailed above, especially vitamin C and/or E, in conventional formulation.

The soft gelatin capsules are produced in a conventional way as described, for example, in the cited texbook by R. Voigt. The specific procedure for this can be as follows:

The shaping, filling and sealing of the capsules expediently takes place in one step. Merely the filling material and the gelatin composition for the capsule shell are made up separately beforehand. For problem-free weighing and dispensing of, in particular, the constituents of the capsule filling it is necessary for them to be free-flowing and pumpable, it being necessary that certain viscosity limits are not exceeded and no inhomogeneities occur, eg. through sedimentation. This is ensured in the soft gelatin capsules according to the invention by using the powdered products with the particle size distribution defined above.

The invention therefore also relates to the use of powdered retinoid, carotenoid and/or vitamin products with a particle size distribution as stated above for the production of soft gelatin capsules.

Conventional substances are used besides the powdered products to form a dispersion or as dispersion auxiliaries in the soft gelatin capsules according to the invention, eg. vegetable oils, lecithins, waxes, and emulsion or dispersion aids.

The composition of the gelatin material for the capsule shell is known per se and, besides the gelatin (about 60–70% by weight), also contains a plasticizer such as glycerol or sorbitol (about 30–40% by weight) and, where appropriate, preservatives, flavorings, coloring matter and/or other auxiliaries as described in EP-A-337 509.

The capsules themselves are preferably produced by the rotary die process in which continuous gelatin ribbons (40% gelatin, 30% glycerol, 30% water) pass between two rolls with dies rotating in opposite directions. The rolls punch the capsule shapes out of the gelatin ribbons. At the same time, the filling material is injected between the two punch blades, and the edges thereof are sealed together by the action of heat. The finished capsule is then ejected, precooled and, after washing, eg. with organic solvent, dried in conditioned air with a relative humidity of about 30% and at 20° C. Different shapes (round, oval, oblong, suppository-, drop- or ampoule-shaped) can be produced without difficulty. The capsules can be produced to have one or two colors. This process is described in detail in the textbook by R. Voigt (loc. cit., page 232).

EXAMPLE

A capsule filling was produced by mixing the following constituents: 50 parts by weight of a powdered product comprising 5 parts by weight of β-carotene and 45 parts by weight of a gelatin/carbohydrate mixture, 50 parts by weight of vitamin C (German Pharmacopeia), 3 parts by weight of soybean lecithin, 12 parts by weight of D,L-α-tocopherol acetate, 50 parts by weight of medium chain-length triglycerides (German Pharmacopeia) and 32 parts by weight of hard fat (German Pharmacopeia).

The powdered product premixed with soybean lecithin and triglycerides was pumpable and showed no sedimentation of the solid constituents.

The material for the capsule shell was produced separately by mixing the following constituents: 200 parts by weight of gelatin, 55 parts by weight of glycerol, 60 parts by weight of a 70% aqueous sorbitol solution. For coloring the shell material, 1 part by weight of a mixture of $TiO_2$ and a 20% strength β-carotene fatty dispersion was also added.

Soft gelatin capsules in the form of oblong capsules were produced from the capsule filling composition and the shell material by the rotary die process described above. The total weight of the capsules was 950 mg.

The bioavailability of the β-carotene dry powder used as active ingredient is evident from the following test:

Feeding Test on Calves

The test products were administered to groups of 10 milk-fed calves of the same breed and weight in a single dose of 6 mg of β-carotene/kg of body weight. The shape of the curve of the β-carotene level in the blood over the 11 days following the administration was analyzed. The bioavailability emerges from a comparison of the areas under the curves.

Relative Bioavailability in Calves (dispersion=100%)

| β-Carotene dispersion 30% | 100 |
| β-Carotene dry powder 10% | 819 |

We claim:

1. a soft gelatin capsule consisting of capsule shell and capsule filling, wherein the capsule filling comprises one or more water-insoluble active ingredient(s) in the form of a liquid dispersion of a powdered product having the following particle size distribution: <10% <5 μm and <1% >400 μm.

2. A soft gelatin capsule as claimed in claim 1, wherein the powdered product has the following particle size distribution: <10% <10 μm and <1% >350 μm.

3. A soft gelatin capsule as claimed in claim 1, wherein the powdered product contains the water-insoluble active ingredient(s) and a colloid.

4. A soft gelatin capsule as claimed in claim 1, wherein the water-insoluble active ingredient(s) is (are) selected from the group consisting of retinoids, carotenoids and/or vitamins.

5. A soft gelatin capsule as claimed in claim 3, wherein the colloid is a gelatin/carbohydrate matrix.

6. A soft gelatin capsule as claimed in claim 4, wherein the carotenoid is β-carotene.

7. A soft gelatin capsule as claimed in claim 1, which, besides the powdered products, also comprises other active ingredients in a conventional formulation, in particular vitamins such as, especially, vitamin C and/or E.

8. The use of powdered retinoid, carotenoid and/or vitamin products with a particle size distribution as claimed in claim 1 for the production of soft gelatin capsules.

* * * * *